United States Patent [19]  [11] 3,966,851
Feasey et al.  [45] June 29, 1976

[54] PHENOL PRECURSORS

[75] Inventors: Ronald George Feasey, Knebworth; John Brewster Rose, Letchworth, both of England

[73] Assignee: Imperial Chemical Industries Limited, London, England

[22] Filed: July 19, 1974

[21] Appl. No.: 490,101

Related U.S. Application Data

[62] Division of Ser. No. 165,769, July 15, 1971, Pat. No. 3,840,580.

[30] Foreign Application Priority Data

| July 15, 1970 | United Kingdom | 34308/70 |
| July 15, 1970 | United Kingdom | 34309/70 |
| Aug. 6, 1970 | United Kingdom | 37949/70 |
| Dec. 23, 1970 | United Kingdom | 61171/70 |

[52] U.S. Cl. .............................. 260/949; 260/946; 260/968
[51] Int. Cl.² ........................................... C07F 9/14
[58] Field of Search ................. 260/946, 949, 329.3, 260/346.2 M, 968

[56] References Cited

UNITED STATES PATENTS

| 3,083,201 | 3/1963 | Anderson | 260/346.2 M X |
| 3,153,663 | 10/1964 | Sirrenberg et al. | 260/949 X |
| 3,341,552 | 9/1967 | Cornell | 260/329.3 |
| 3,770,832 | 11/1973 | Leslie et al. | 260/329.3 X |
| 3,819,650 | 6/1974 | Hofer et al. | 260/329.3 |

OTHER PUBLICATIONS

Houben-Weyl, Methoden der Organischen Chemie, vol. IX (1955) pp. 240, 241.

*Primary Examiner*—Richard L. Raymond
*Attorney, Agent, or Firm*—Cushman, Darby & Cushman

[57] ABSTRACT

Phenol precursors are provided having the formula $(Q'ZQO)_mY$ in which Q is a bivalent aromatic radical, Q' is a univalent aromatic radical or the moiety of a bivalent aromatic radical, Z is $-SO_2-$, $-SO-$, $-CO-$ or $-CH_2-$, Y is $-CO-$ or $-POCl_2$ and $m$ is an integer having the value 1 when Y is $-POCl_2$ and the value 2 when Y is $-CO-$.

4 Claims, No Drawings

PHENOL PRECURSORS

This is a division, of application Ser. No. 165,769 filed July 15, 1971, now U.S. Pat. No. 3,840,580.

This invention relates to novel phenol precursors.

A Friedel-Crafts condensation reaction on an aromatic compound is hindered and may even be inhibited by the presence in the aromatic compound of an electron-deficient group or a group that is able to react with the Friedel-Crafts catalyst. For instance, the presence of a phenolic group causes retardation of the condensation reaction because of the facility with which the phenol can form salts with the catalyst. We have now found that phenol precursors which can be converted to the corresponding phenol can be prepared by a Friedel-Crafts condensation reaction.

According to the present invention, phenol precursors are provided having the formula $(Q'ZQO)_mY$ in which Q is a bivalent aromatic radical, Q' is a univalent aromatic radical or the moiety of a bivalent aromatic radical, Z is $-SO_2-$, $-SO-$, $-CO-$ or $-CH_2-$, Y is $-CO-$ or $-POCl_2$ and $m$ is an integer having the value 1 when Y is $-POCl_2$ and the value 2 when Y is $-CO-$.

Phenol precursors of the invention may be prepared by a process which comprises reacting together under Friedel-Crafts conditions a first compound having the formula $(A-Q-O)_mY$ in which Q is a bivalent aromatic radical, Y is $-CO-$ or $-POCl_2$ and $m$ is an integer having the value 1 when Y is $-POCl_2$ and the value 2 when Y is $-CO-$, with a second compound having the formula $(Q'B)_n$ in which $n$ is an integer having the value 1 or 2, Q' is a univalent aromatic radical when $n$ is 1 or the moiety of a bivalent aromatic radical when $n$ is 2, and one of A and B is a hydrogen atom and the other of A and B is a group of the formula $-Z-X$ in which Z is $-SO_2-$, $-SO-$, $-CO-$ or $-CH_2-$ and X is chlorine or bromine, the approximate molar ratio of the first compound $(A-Q-O)_mY$ to the second compound $(Q'B)_n$ being 1:1 when $m$ and $n$ are both 1 or both 2, being 1:2 when $m$ is 2 and $n$ is 1 and being 2:1 when $m$ is 1 and $n$ is 2. The phenol precursors according to the invention thus have the formula $(Q'-Z-Q-O-)_mY$ and may have the following structures:

| ratio of first compound to second compound | Structure of product |
| --- | --- |
| 1 : 1 | Q'—Z—Q—O—POCl$_2$ |
| 1 : 2 | (Q'—Z—Q—O—)$_2$CO |
| 2 : 1 | (Q'—Z—Q—O—POCl$_2$)$_2$ |
| 2 : 2 | polymer having repeating units of the formula $\{Q'-Z-Q-O-CO-O-Q-Z-O'\}$ |

The aromatic radical Q may be any bivalent aromatic radical. The aromatic radical Q' may be any univalent aromatic radical when $n$ is 1 or the moiety of a bivalent aromatic radical when $n$ is 2. By the expression "moiety of a bivalent aromatic radical" we mean an equal half of that radical. The aromatic radical may be derived from an aromatic hydrocarbon such as for example benzene, biphenyl, naphthalene, indene, anthracene, fluorene, acenaphthene, phenanthrene and chrysene, or from a polynuclear hetero-aromatic compound such as for example dibenzofuran and dibenzothiophen.

Preferred aromatic radicals are those derived from benzene, biphenyl and naphthalene.

The aromatic radicals may be substituted by any atom or group which is inert to the reaction conditions. Examples are halogen atoms and alkyl and alkoxy groups containing up to ten carbon atoms. The aromatic radical not containing the hydrogen atom which is eliminated by the condensation reaction may also contain substituents which tend to deactivate the aromatic ring. Examples of such groups are nitro, aldehyde, ketone, nitrile or sulphone.

One of groups A and B is a hydrogen atom which is eliminated on condensation with the group X included in the other of group A and B. Group X may be chlorine or bromine of which chlorine is preferred. The other of group A and B is either $-COX$, $-SOX$, $-SO_2X$ or $-CH_2X$. Groups $-COX$ and $-SO_2X$ are preferred groups.

The Friedel-Crafts condensation reaction and the general conditions are well known (Encyclopaedia of Chemical Technology, Kirk-Othmer, John Wiley, New York 1966, pages 135 to 166). The reaction may be considered as the combining of two chemical compounds through the formation of carbon-to-carbon or carbon-to-sulphur bonds under the influence of a Lewis acid as catalyst. Such a reaction may therefore fall within the three categories, alkylation, acylation and sulphonylation. In the process of the invention, we consider the formation of chemical bonds through the reaction of the $-COX$, $-SOX$, $-SO_2X$ and $-CH_2X$ groups. A particular advantage of the process of the invention is that the Friedel-Crafts catalyst need only be present in small amounts; that is to say, a concentration of less than the molar concentration of the reactant containing the halogen atom to be replaced. The catalyst should be essentially anhydrous and convenient examples include aluminium chloride, ferric chloride, indium trichloride, antimony pentachloride, tin tetrachloride, boron trifluoride and zinc chloride. Ferric chloride and indium trichloride are preferred catalysts.

As with most chemical reactions, a compromise has to be reached between obtaining essentially a single product by performing the reaction at ambient temperature over a long period of time or carrying out the reaction at higher temperatures over a shorter reaction time with attendant risk of a multiplicity of products and product degradation. Accordingly, the condensation reaction of the present invention may be carried out at temperatures between ambient and 200°C, a preferred range being 100°C to 160°C. Within such a range of temperature, the bulky carbonate or phosphorochloridate group usually restricts condensation to the para-position of the aromatic residue. The reaction may be carried out in an atmosphere of air although the presence of an inert atmosphere, for example nitrogen, is preferred.

The condensation reaction may be carried out either in the absence or presence of a diluent. If no diluent is present, it is preferable that at least one reactant melts at a temperature lower than the temperature at which the reaction is carried out. It is however, desirable to carry out the reaction in the presence of a diluent which is inert to the reaction. Examples of such diluents are s-tetrachloroethane, chlorinated biphenyls sold as "Arochlor" (Trade Mark), dimethyl sulphone, tetramethylene sulphone, 1-nitropropane and nitrobenzene. A preferred diluent is nitrobenzene. Alternatively, the reaction can be carried out in the presence of an excess of one of the reactants as solvent, for example benzene, chlorobenzene, or 1,2-, 1,3-, or 1,4-dichlorobenzene.

The phenol precursor may be isolated and purified from the reaction mixture, for example by filtration followed by recrystallisation. A particular use of the invention is in the preparation of substituted precursors to be subsequently converted into substituted phenols. The conversion may be carried out by cleavage of the carbonate or phosphorochloridate using a base, conveniently an alkali metal hydroxide in alcoholic solution, to produce the corresponding phenate, followed by acidification, conveniently by dilute mineral acid, to precipitate the substituted phenol. The phenol may then be washed, conveniently with methanol or ethanol, and may be used wet or may be dried before further use. Bis-(arylphosphorochloridates) and the corresponding polymeric carbonates of the invention may similarly be converted into the corresponding bisphenol.

Substituted phenols so formed may be used as precursors in the preparation of dyestuffs, antioxidants or drugs. They may also be used as starting materials for the manufacture of polymers, such as for example those described in British patent specification No. 1,153,035 where for example a polymer having repeat units of the formula

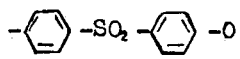

is prepared by the condensation of the alkali metal salt of 4-chlorophenylsulphonyl phenol. This phenol may be made from a phenol precursor of the present invention.

Alternatively, polymers of the type described in British patent specification No. 1,153,035 may be prepared from the phenol precursors of the invention without isolation of the substituted phenols and subsequent polymerisation by carrying out the cleavage and polymerisation reactions consecutively in situ.

The invention is illustrated by the following examples.

EXAMPLE 1

Diphenyl carbonate (21.4 g; 0.10 mole), 4-chlorobenzene sulphonyl chloride (42.2 g; 0.20 mole), anhydrous ferric chloride (ca. 0.3 g) and nitrobenzene (150 cm³) were stirred together under nitrogen at 150°C for 5 hours whilst hydrogen chloride was evolved. The reaction mixture was allowed to cool, was diluted with nitrobenzene and then filtered. The solid which was collected was washed with methanol and dried in vacuo to a white powder (30.7 g).

A small portion of the powder was recrystallised from chloroform to yield a white, crystalline material, melting point (m.p.) 200°–202°C. The infra-red and nuclear magnetic resonance (nmr) spectra of the compound were consistent with bis-[4-(4-chlorophenylsulphonyl)phenyl]carbonate (structure I).

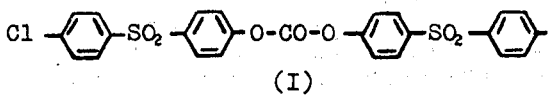

(I)

A further portion (11.26 g) of the white powder was stirred with refluxing alcoholic potassium hydroxide (10.6 g; 0.16 mole potassium hydroxide pellets in 50 cm³ ethanol) for 2 hours. The mixture was acidified and the precipitate was collected, washed with water and dried to a white powder (9.83 g). This material had m.p. 147°–150°C and gave an infra-red spectrum consistent with its being 4-chloro-4'-hydroxydiphenyl sulphone.

A final portion (11.26 g) of the white powder was stirred with refluxing alcoholic potassium hydroxide (6.6 g; 0.10 mole potassium hydroxide pellets in 50 cm³ ethanol) for 1.5 hours. The mixture was filtered hot and allowed to cool whereupon crystals (5.5 g) deposited which were collected and dried in vacuo. Potentiometric titration of the crystals against acid showed them to have an equivalent weight of 309, consistent with their being pure potassium salt of 4-chloro-4'-hydroxydiphenyl sulphone (calculated equivalent weight 307.5). A portion of the crystals (ca. 1 g) was heated at 280°C in vacuo for 0.75 hour and the resulting polymeric product was dissolved in dimethyl formamide, reprecipitated in ethanol and dried to yield a polymer (0.53 g) which had reduced viscosity 0.43, as measured at 25°C on a solution in dimethyl formamide containing 1 g polymer in 100 cm³ of solution (1% w/v).

EXAMPLE 2

Chlorosulphonic acid (39.6 cm³; 0.6 mole) was dripped onto stirred diphenyl carbonate (21.4 g; 0.1 mole). Hydrogen chloride was evolved and the resulting solution was heated to 80°C for 2.5 hours and then allowed to cool. The reaction mixture was poured into ice/water and the resulting suspension was extracted with methylene chloride. The methylene chloride solution was evaporated to yield a crude product (16.2 g) which was recrystallised from 1,2-dichloroethane/petrol to yield a white, crystalline compound (13.8 g) which had m.p. 148.5°–150°C and mass and infra-red spectra consistent with bis-(4-chlorosulphonylphenyl)-carbonate (structure II).

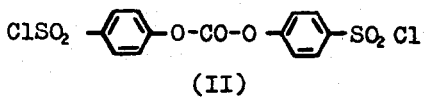

(II)

A portion (2.1 g) of the crystalline compound was stirred with chlorobenzene (1.1 g; 0.010 mole), nitrobenzene 3 cm³) and anhydrous ferric chloride (ca. 0.1 g) at 140°C under nitrogen for 6.5 hours. The reaction mixture was poured into methanol and the precipitate was collected, dried and recrystallised from 1,2-dichloroethane. The resulting crystals were shown to be identical with the compound assigned structure I in example 1 by mixed melting point determinations and by comparison of infrared spectra; the crystals were also converted into a compound identified by its infrared spectrum as 4-chloro-4'-hydroxydiphenyl sulphone by hydrolysis in ethanolic potassium hydroxide, as described in example 1.

EXAMPLE 3

Bis-(4-chlorosulphonylphenyl) carbonate (4.2 g; 0.01 mole), 4-(4-chlorophenyl sulphonyl) biphenyl (6.6 g; 0.02 mole), anhydrous ferric chloride (ca. 0.3 g) and nitrobenzene (30 cm³) were stirred together under nitrogen at 140°C for 6 hours whilst hydrogen chloride was evolved. The reaction mixture was allowed to cool and was then poured into methanol. The white solid which deposited was collected, washed with methanol and dried in vacuo to a white powder (7.4 g) whose infra-red spectrum was consistent with the structure III.

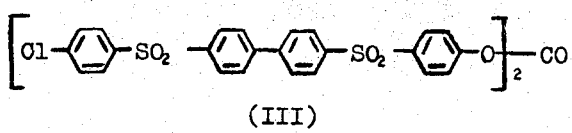

A portion (5.0 g) of the white powder was stirred with refluxing alcoholic potassium hydroxide (6.6 g; 0.10 mole potassium hydroxide pellets in 50 cm³ ethanol) for 2–3 minutes. The resulting solution was diluted with water, acidified, and extracted with dichloromethane. The dichloromethane solution was evaporated to yield crystals of a material, virtually identical in melting point (244°–248°C) and infra-red spectrum with an authentic sample of 4-(4-chlorophenyl sulphonyl)-4'-(4-hydroxy phenyl sulphonyl) biphenyl.

A portion (1.52 g) of the crystals was dissolved in hot alcoholic potassium hydroxide (0.24 g; 0.0036 mole potassium hydroxide pellets in 10 cm³ ethanol) and the resulting golden-yellow solution was allowed to cool. Pale yellow crystals (1.3 g) precipitated which were collected, washed with ice-cold ethanol and, together with the potassium salt of 4-fluoro-4'-hydroxyphenyl sulphone (1.3 g), were heated to 300°C during 40 minutes. The resulting polymeric material was dissolved in dimethyl formamide, precipitated in methanol and dried to yield a copolymer comprising about 70% of units of the structure IVa and about 30% of units of the structure IVb

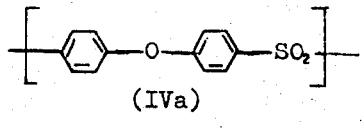

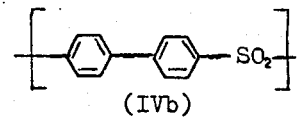

which had reduced viscosity 0.90, measured at a 1% w/v solution in dimethyl formamide at 25°C.

EXAMPLE 4

Into a 500 cm³ flask were placed bis-(1-naphthyl) carbonate (48 g; 0.113 mole) and a solution of 4-chloronaphthalene-1-sulphonyl chloride (74 g, 0.286 mole) in nitrobenzene (100 cm³). The mixture was warmed to 100°C and anhydrous ferric chloride (1 g) was added. The mixture was stirred and when the evolution of hydrogen chloride slowed down the temperature was increased to 120° and the reaction was kept at this temperature for 2 hours. The contents of the flask were then poured into methanol (1 dm³) to give an oil which was separated from the methanolic liquors, washed with methanol (500 cm³), and then a methanolic solution of potassium hydroxide added (1 dm³ of 2 normal). On warming to 50°C the oil dissolved to give an orange solution which was diluted with water (1 dm³) and concentrated hydrochloric acid (200 cm³) carefully added. A white precipitate formed which was filtered off, dried, and on recrystallisation from a mixture of methyl ethyl ketone and petroleum (b.p. 60°–80°C) afforded 4-chloro-4'-hydroxydinaphthyl-1,1'-sulphone (45 g; 62%) m.p. 280°–281°C. The infra-red and nmr spectra were consistent with that compound.

EXAMPLE 5

Diphenyl carbonate (21.42 g; 0.10 mole), 4-nitrobenzoyl chloride (37.10 g; 0.20 mole), anhydrous ferric chloride (about 0.3 g) and nitrobenzene (40 cm³) were stirred together at 140°C under a stream of nitrogen for 17 hours, whilst hydrogen chloride was evolved. The reaction mixture was poured into methanol (about 200 cm³) and the precipitate which formed was collected, washed with methanol and partially dried to yield bis-(4-(4'-nitrobenzoyl)phenyl) carbonate (57.8 g), wet with methanol.

A portion (25.6 g) of the wet carbonate, potassium hydroxide (11.2 g; 0.2 mole) and ethanol were brought to reflux and the resulting mixture was diluted with water to give a clear red solution. The solution was poured into an excess of dilute hydrochloric acid and a precipitate formed which was collected, washed with water and recrystallised from aqueous ethanol to yield 4-hydroxy-4'-nitrobenzophenone (17.0 g; corresponding to a 79% yield based upon starting materials) which had a melting point of 191°–194°C. The infra-red and nmr spectra of the product were consistent with its being substantially pure.

EXAMPLE 6

Bis-(4-chlorosulphonylphenyl) carbonate (4.20 g; 0.01 mole), diphenyl carbonate (2.14 g; 0.01 mole), anhydrous ferric chloride (about 0.2 g) and nitrobenzene (10 cm³) were stirred together under a stream of nitrogen at 140°C for 18 hours, whilst hydrogen chloride was evolved. The resulting viscous solution was poured into stirred methanol and the precipitate which was poured was collected, extracted with hot methanol and dried to yield poly(diphenylene carbonate sulphone) (5.8 g; V).

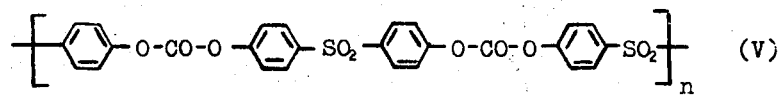

When treated with ethanolic potassium hydroxide solution at reflux, this polymer was rapidly hydrolysed to the dipotassium salt of bis-(4-hydroxyphenyl)sulphone.

EXAMPLE 7

Bis-(4-chlorosulphonylphenyl) carbonate (65.76 g; 0.16 mole), biphenyl (24.64 g; 0.16 mole), anhydrous ferric chloride (0.8 g; 0.005 mole) and nitrobenzene (80 cm³) were charged to a round-bottom flask fitted with a stirrer, nitrogen, inlet, and outlet via a reflux condenser. The reaction mixture was stirred, maintained at 150°C for 4 hours, whilst hydrogen chloride was evolved, and then allowed to cool. The resulting viscous solution was slowly poured into vigorously stirred methanol (1 dm³) and the solid which precipitated was thoroughly washed with methanol and then dried to yield polymer (68.5 g; 87% of theoretical yield) having repeat units of the structure:

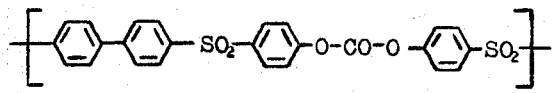

The polymer was added to a solution of potassium hydroxide pellets (52.8 g; 0.80 mole) in ethanol (200 cm³). The resulting mixture was heated to reflux for ¾ hour and then allowed to cool whilst yellow needles precipitated. The yellow needles were dissolved in water (600 cm³) and the resulting solution was acidified with concentrated hydrochloric acid solution. The white precipitate which formed was collected, washed with water and dried to yield crude bis-4-(4-hydroxyphenylsulphonyl) biphenyl (52.8 g; 71% of theoretical yield). This crude material was recrystallised from aqueous ethanol to yield colourless plates of bis-4-(4-hydroxyphenylsulphonyl) biphenyl (35.4 g; 47% yield; VI), m.p. 246°–247.5°C.

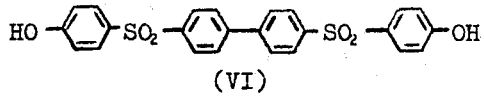

EXAMPLE 8

Bis-(4-biphenyl) carbonate (439.2 g; 1.20 mole), 4-chlorobenzene sulphonyl chloride (557.1 g; 2.64 mole), anhydrous ferric chloride (12.0 g; 0.074 mole) and nitrobenzene (600 cm³) were stirred together for 4 hours at 120°C under a stream of nitrogen whilst hydrogen chloride evolved from the reaction mixture. The reaction mixture was allowed to cool and was then diluted with methanol (750 cm³). The solid which precipitated was collected, washed with methanol and dried to yield bis-4-[4-(4-chlorophenylsulphonyl) biphenyl] carbonate (725 g; VII)

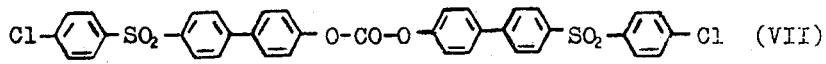

Bis-4-[4-(4-chlorophenylsulphonyl)biphenyl] carbonate (715.0 g; 1.01 mole), aqueous potassium hydroxide solution (557.3 g; 4.85 mole) and ethanol (2250 cm³) were stirred under reflux for 2½ hours. The resulting slurry was diluted with methanol until a clear solution was obtained which was added to an excess of a mixture of concentrated hydrochloric acid and water (1:1 v/v). A precipitate formed which was collected, washed with methanol, dried and recrystallised from aqueous dimethyl formamide to yield 4-(4-chlorophenylsulphonyl)-4'-hydroxy biphenyl (352 g) which had melting point 268°–270°C.

4-(4-chlorophenylsulphonyl)-4'-hydroxy biphenyl (34.45 g; 0.10 mole), anhydrous potassium fluoride (12.20 g; 0.21 mole) and sulpholane (60 g) were stirred together under nitrogen at 265°C for 18 hours. The resulting viscous solution was cooled to 160°C, diluted with sulpholane (70 cm³) and saturated with gaseous methyl chloride for 1 hour. The solution was then cooled, diluted with dimethyl formamide until mobile, filtered and then poured into vigorously stirred methanol. The polymer which precipitated was collected, extracted with hot water then hot methanol-acetone mixture (3:2 v/v) and dried to yield a polymer having repeat units of the structure

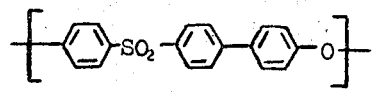

which had reduced viscosity 0.55 (measured as a 1% w/v solution in dimethyl formamide at 25°C) and which was extruded at 380°C to form a pale amber lace.

A sample (35.7 g; 0.05 moles) of bis-4-[4-(4-chlorophenyl sulphonyl) biphenyl] carbonate, aqueous potassium hydroxide solution (22.94 g containing 0.20 moles of potassium hydroxide) and 1,1-dioxothiolan (sulpholane) (150 cm³) were charged to a round bottom flask (capacity 1 dm³) equipped with a dry nitrogen inlet, stainless steel stirrer and a vacuum distillation head, condenser and receiver. The flask was pumped with nitrogen, pressure reduced to 1.0 kN/m² (7 mm of mercury) and the temperature of the stirred mixture allowed to rise slowly. As the temperature rose, water distilled from the reaction mixture first, followed by 1,1-dioxothiolan. When about 50 cm³ of 1,1-dioxothiolan had distilled, the pressure within the flask was returned to atmospheric and the temperature increased to 200°C. The mixture was stirred at this temperature for 1.5 hours during which it became more viscous. The mixture was then dripped into vigorously stirred methanol and the polymer which precipitated was collected, extracted three times with boiling methanol-acetone mixture (1:1 volume/volume), twice with boiling water-methanol mixture (1:1 volume/volume) and then dried. The resulting polymer had repeat units of the structure

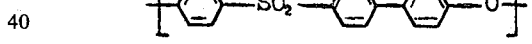

and a reduced viscosity of 0.44 (measured as a 1% w/v solution in dimethyl formamide at 25°C).

EXAMPLE 9

4-Hydroxybiphenyl (170.2 g; 1.00 mole), phosphoryl chloride (91.6 cm³; 1.00 mole), anhydrous aluminium chloride (1.33 g; 0.01 moles) and nitrobenzene were stirred together under nitrogen for 2.5 hours at 110°C whilst hydrogen chloride was evolved. To the resulting solution of biphenyl-4-phosphorochloridate was added 4-chlorobenzene sulphonyl chloride (211.0 g; 1.00 mole) and anhydrous ferric chloride (12.0 g; 0.07 moles). The temperature of the reaction mixture was raised to 160°C and stirring was continued for a further 19 hours whilst further evolution of hydrogen chloride occurred. The reaction mixture was poured into methanol and the precipitate collected, dried and then stirred with refluxing alcoholic potassium hydroxide (46.2 g; 0.70 moles potassium hydroxide pellets in 175 cm³ ethanol) for 5 hours. Water was added to the mixture to give a clear solution which was acidified with concentrated hydrochloric acid. The precipitate which formed (83 g) was collected, dried and then recrystallised from dimethyl formamide and 1,2-dichloroethane/dimethyl sulphoxide to constant melting point (270°–271°C). The resulting white crystalline solid had equivalent weight 345 and an infra-red spectrum virtually identical with an authentic sample of 4-(4-chlorophenyl sulphonyl)-4'-hydroxybiphenyl.

A portion of the crystalline solid (3.45 g), aqueous potassium hydroxide (2.5 cm³ of a 4N solution; 0.010 moles) and sulpholane (20 cm³), were placed in the flask of a rotary evaporator. The resulting mixture was evaporated to dryness under pressure of 1mm of mercury and at a temperature rising to 260°C, and the yellow residue was then heated in vacuo for 30 minutes at between 280°C and 320°C. The polymeric reaction produce was dissolved in dimethyl formamide, precipitated into methanol and dried to yield polymer (1.9 g) of the structure I, which had reduced viscosity 0.52 (measured at 25°C on a solution in dimethyl formamide containing 1g polymer in 100 cm³ of solution)

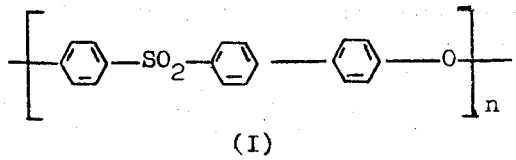

(I)

and a glass-to-rubber transition temperature of 270°C (measured by differential scanning calorimetry at a heating rate of 16 deg C/min). The polymer was compression moulded at 350°C, and also cast from concentrated dichloromethane solution, into films which could be creased repeatedly without fracture.

EXAMPLE 10

4-Chlorosulphonylphenyl phosphorochloridate (1.32 g; 0.0042 moles), 4-(4-chlorophenylsulphonyl) biphenyl (1.37 g; 0.0042 moles), nitrobenzene (10 cm³) and anhydrous ferric chloride (ca. 0.3 g) were stirred together under nitrogen for 24 hours at 140°C whilst hydrogen chloride was evolved. The reaction mixture was poured into methanol (200 cm³) and the precipitate (2.5 g) was collected and dried.

A portion (2.2 g) of this material was stirred with refluxing alcoholic, potassium hydroxide (2.8 g; 0.042 moles potassium hydroxide pellets in 25 cm³ ethanol) for 1 hour. The resulting mixture was diluted with water, filtered, and the filtrate acidified with concentrated hydrochloric acid. A precipitate formed which was collected, washed with methanol and dried to yield 4-(4-chlorophenylsulphonyl)-4'-(4-hydroxyphenylsulphonyl) biphenyl (1.7 g).

EXAMPLE 11

Bis-(4-biphenylyl) carbonate (16.7 g; 0.045 moles), 4-chlorobenzoyl chloride (17.3 g; 0.099 moles), nitrobenzene (50 cm³) and anhydrous ferric chloride (ca 1 g) were stirred together at 140°C under a stream of nitrogen for 3 hours during which time hydrogen chloride (0.093 moles) was evolved. Acetyl acetone (2 cm³) was added to the reaction mixture which was then allowed to cool.

Methanol (100 cm³) was added to the stirred mixture and the suspended solid was collected, washed with methanol and dried. The crude product (22.2 g) was recrystallised from a mixture of 1,2-dichloroethane (200 cm³) and dimethyl formamide (50 cm³) to yield a solid (18.2 g) having a melting point of 292°–294°C and infra-red and mass spectra consistent with the solid being bis-[4-(4-chlorobenzoyl)-biphenylyl] carbonate,

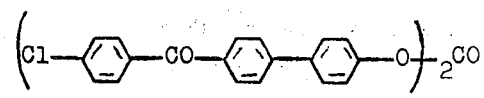

Bis-[4-(4-chlorobenzoyl)-biphenylyl] carbonate (17.3 g; 0.0269 moles), potassium hydroxide pellets (8.88 g; 0.1345 moles) and ethanol (66 cm³) were stirred together at reflux for 2 hours. The resulting orange-red paste was diluted with water (60 cm³) until a clear solution was obtained which was acidified whilst still hot by the addition of a hydrochloric acid (6 normal; 40 cm³). The mixture was cooled and the precipitate collected, washed with water and recrystallised from a mixture of ethanol (350 cm³) and methyl ethyl ketone (50 cm³) and then from 1,2-dichloroethane to yield a product having melting-point 197.5°–198.5°C, infra-red, n.m.r., and mass spectra and elemental analysis (Found: carbon 73.7%; hydrogen 4.4 %; Calculated: carbon 73.9%; hydrogen 4.3%) consistent with its being 4-(4-chlorobenzoyl)-4'-hydroxy biphenyl

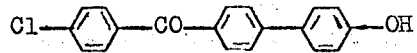

Bis-[4-(4-chlorobenzoyl)-biphenylyl] carbonate (16.1 g; 0.025 moles), bis-[4-(chlorobenzenesulphonyl)-biphenylyl] carbonate (17.9 g; 0.025 moles), dimethyl sulphoxide (125 cm³), diphenyl sulphone (125 g) and aqueous potassium hydroxide solution (22.94 g; 0.20 moles) were charged into a flask fitted with a stirrer, dry nitrogen, inlet and a vacuum distillation head, condenser and receiver. Water and then dimethyl sulphoxide were distilled from the reaction mixture as the temperature was raised to 180°C and the pressure reduced to 140 N/m² (1 mm of mercury). The pressure was maintained and the temperature raised to 215°C when diphenyl sulphone began to reflux. The pressure in the flask was returned to atmospheric by the admission of nitrogen and the reaction mixture heated to 220°C for 16 hours and at 265°C for a further 3 hours.

The stirred mixture was then allowed to cool to 150°C when dimethyl formamide (300 cm³) was added. The resulting slurry was poured into methanol (500 cm³) and the solid collected, extracted with boiling methanol, water, water-acetone (1:1 v/v) and methanol-acetone (1:1 v/v) and finally dried to yield a copolymer (25.8 g) consisting essentially of equal proportions of repeat units having the formula

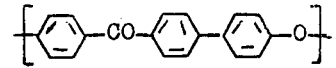

and

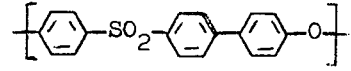

The copolymer had reduced viscosity of 1.26 as measured at 25°C in concentrated sulphuric acid (1% w/v) and was compression-moulded at 400°C into film which could be creased repeatedly without fracture.

Homopolymer consisting essentially of repeat units having the structure

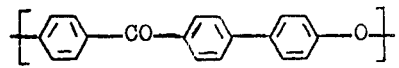

could be made by a similar method.

EXAMPLE 12

Diphenyl carbonate (107.0 g; 0.50 moles), 4-chlorobenzoyl chloride (192.5 g; 1.10 moles), nitrobenzene (250 cm³) and anhydrous ferric chloride (9.72 g; 0.06 moles) were stirred together under a stream of dry nitrogen and heated to 150°C over 30 minutes. The reaction mixture was then maintained at this temperature for 18 hours, by the end of which time a total of 0.980 moles of hydrogen chloride had evolved. Acetyl acetone (50 cm³) was added to the reaction mixture which was then allowed to cool.

Methanol (500 cm³) was added to the stirred mixture and the suspended solid was collected, washed with methanol and dried. The crude product (155 g) was recrystallised from 1,2-dichloro-benzene (1 dm³) to yield bis-[4-(4-chlorobenzoyl) phenyl] carbonate (138 g) which had melting point 235°–237°C and an infrared spectrum consistent with its expected structure.

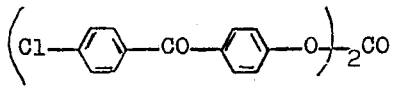

Bis-[4-(4-chlorobenzoyl)-phenyl] carbonate could be hydrolysed to 4-chlorobenzoylphenol and polymerised by the method described in Example 11 with bis-[4-(4-chlorophenylsulphonyl) phenyl] carbonate to give polymer having repeat units of the formula

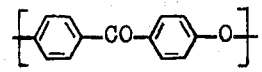

and

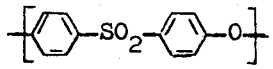

What we claim is:

1. A phenol precursor having the formula Q'Z-QOPOCl₂ in which Q is a bivalent aromatic radical selected from the group consisting of unsubstituted phenylene, biphenylylene and naphthylene radicals and substituted radicals derived therefrom and Q' is a univalent aromatic radical selected from the group consisting of unsubstituted phenyl, biphenylyl and naphthyl radicals and substituted radicals derived therefrom, the substituents in the Q and Q' radicals, when substituted, being selected from the group consisting of halogen atoms, alkyl and alkoxy radicals containing up to 10 carbon atoms, and radicals that tend to deactivate an aromatic ring, provided that not more than one of said Q and Q' radicals contains such deactivating substituents, and Z is —SO₂— or —CO—.

2. A phenol precursor according to claim 1 having the formula

3. A phenol precursor according to claim 1 having the formula

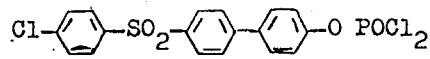

4. A process for the preparation of a phenol precursor having the formula Q'ZQOPOCl₂ in which Q is a bivalent aromatic radical selected from the group consisting of unsubstituted phenylene, biphenylylene and naphthylene radicals and substituted radicals derived therefrom wherein the substituent atoms or groups are inert to the reaction conditions and Q' is a univalent aromatic radical selected from the group consisting of unsubstituted phenyl, biphenylyl and naphthyl radicals and substituted radicals derived therefrom wherein the substituent atoms or groups are inert to the reaction conditions and Z is —SO₂— or —CO—, said process comprising reacting together, under Friedel Crafts conditions, approximately equimolar proportions of a first compound having the formula A—Q—OPOCl₂ and a second compound of the formula Q'B, one of A and B being hydrogen and the other being a group of the formula —Z—X where X is chlorine or bromine.

* * * * *